United States Patent [19]

Mendelson et al.

[11] Patent Number: 5,277,181

[45] Date of Patent: Jan. 11, 1994

[54] NONINVASIVE MEASUREMENT OF HEMATOCRIT AND HEMOGLOBIN CONTENT BY DIFFERENTIAL OPTICAL ANALYSIS

[75] Inventors: Yitzhak Mendelson; Yi Wang; Brian D. Gross, all of Worcester, Mass.

[73] Assignee: VivaScan Corporation, Southboro, Mass.

[21] Appl. No.: 806,144

[22] Filed: Dec. 12, 1991

[51] Int. Cl.⁵ .............................................. A61B 5/00
[52] U.S. Cl. ..................................... 128/633; 128/665; 356/41
[58] Field of Search ................................. 128/633-; 356/39-; 422/82.09

[56] References Cited

U.S. PATENT DOCUMENTS

| | | |
|---|---|---|
| 1,758,088 | 5/1930 | Schmick . |
| 2,721,942 | 10/1955 | Friel et al. ............................ 250/435 |
| 3,463,142 | 8/1969 | Harte .................................... 128/633 |
| 3,614,450 | 10/1971 | Hill et al. ............................. 250/210 |
| 3,638,640 | 2/1972 | Shaw ...................................... 356/41 |
| 3,926,527 | 12/1975 | Pembrook et al. ................. 356/246 |
| 3,958,560 | 5/1976 | March ................................... 356/39 |
| 3,963,019 | 6/1976 | Quandt ................................. 356/39 |
| 4,029,085 | 6/1977 | Dewitt et al. ..................... 128/2 R |
| 4,033,330 | 7/1977 | Willis et al. ........................ 356/39 |
| 4,169,676 | 10/1979 | Kaiser ................................. 128/633 |
| 4,266,554 | 5/1981 | Hamaguri ........................... 128/633 |
| 4,267,844 | 5/1981 | Yamanishi .......................... 128/633 |
| 4,306,877 | 12/1981 | Lubbers ............................. 23/230 R |
| 4,321,930 | 3/1982 | Jobsis et al. ...................... 128/633 |
| 4,380,240 | 4/1983 | Jobsis et al. ...................... 128/633 |
| 4,398,541 | 8/1983 | Pugliese ............................. 128/665 |
| 4,427,889 | 1/1984 | Muller ............................... 250/339 |
| 4,485,820 | 12/1984 | Flower .............................. 128/633 |
| 4,490,845 | 12/1984 | Steinbruegge et al. ............ 250/210 |
| 4,513,751 | 4/1985 | Abe et al. ......................... 128/2 R |
| 4,523,279 | 6/1985 | Sperinde et al. .................. 364/416 |
| 4,570,638 | 2/1986 | Stoddart et al. .................. 128/665 |
| 4,586,513 | 5/1986 | Hamagur ............................ 125/633 |
| 4,603,700 | 8/1986 | Nichols et al. .................... 128/633 |
| 4,621,643 | 11/1986 | New, Jr. et al. ................... 128/633 |
| 4,653,498 | 3/1987 | New, Jr. et al. ................... 128/633 |
| 4,655,225 | 4/1987 | Dahne et al. ...................... 128/633 |
| 4,694,833 | 9/1987 | Hamaguri ........................... 128/633 |
| 4,704,029 | 11/1987 | Van Heuvelan ..................... 356/39 |
| 4,714,080 | 12/1987 | Edgar, Jr. et al. ................ 128/633 |
| 4,725,147 | 2/1988 | Stoddart ........................... 356/433 |
| 4,750,496 | 6/1988 | Reinhart et al. .................. 128/635 |
| 4,759,369 | 7/1988 | Taylor .............................. 128/633 |
| 4,768,516 | 9/1988 | Stoddart et al. .................. 128/665 |
| 4,785,814 | 11/1988 | Kane . |
| 4,796,636 | 1/1989 | Branstetter et al. ............... 128/33 |
| 4,805,623 | 2/1989 | Jobsis ............................... 128/633 |

(List continued on next page.)

FOREIGN PATENT DOCUMENTS

| | | |
|---|---|---|
| 0074428 | 3/1983 | Fed. Rep. of Germany . |
| 0407992 | 1/1991 | Japan . |
| 0152979 | 8/1985 | Netherlands . |

(List continued on next page.)

OTHER PUBLICATIONS

R. A. Peura and Y. Mendelson, "Blood Glucose Sensors: An Overview IEEE/NSF Symposium on Biosensors," pp. 63-68 (1984).

Donahoe and Longini, "A New Noninvasive Backscattering Oximeter," *Proc. IEEE/Seventh Annual Conf. Eng. in Medicine and Biology Society*, pp. 144-147 (1985).

(List continued on next page.)

*Primary Examiner*—Kyle L. Howell
*Assistant Examiner*—Angela D. Sykes
*Attorney, Agent, or Firm*—Hamilton, Brook, Smith & Reynolds

[57] ABSTRACT

The present invention relates to the noninvasive measurement of blood hematocrit and hemoglobin content using differential optical absorption of two or more wavelengths of light during blood volume changes. The method is also useful for noninvasive measurements of other blood analytes, such as glucose, where variations in hematocrit or blood hemoglobin concentration cause errors in the measurement.

12 Claims, 2 Drawing Sheets

U.S. PATENT DOCUMENTS

| | | | |
|---|---|---|---|
| 4,817,623 | 4/1989 | Stoddart et al. | 128/665 |
| 4,832,484 | 5/1989 | Aoyagi et al. | 356/41 |
| 4,854,699 | 8/1989 | Edgar, Jr. . | |
| 4,863,265 | 9/1989 | Flower et al. | 356/41 |
| 4,867,557 | 9/1989 | Takatani et al. . | |
| 4,882,492 | 11/1989 | Schlager | 250/346 |
| 4,907,594 | 3/1990 | Muz | 128/633 |
| 4,927,264 | 5/1990 | Shiga et al. | 356/41 |
| 5,028,787 | 7/1991 | Rosenthal et al. | 250/341 |
| 5,054,487 | 10/1991 | Clarke . | |
| 5,167,230 | 12/1992 | Chance | 128/633 |
| 5,190,040 | 3/1993 | Aoyagi | 128/633 |

FOREIGN PATENT DOCUMENTS

| | | |
|---|---|---|
| PCT/US90-00394 | 1/1990 | PCT Int'l Appl. . |
| WO90/04353 | 5/1990 | PCT Int'l Appl. . |
| WO91/15991 | 10/1991 | PCT Int'l Appl. . |
| 0160768 | 4/1984 | Switzerland . |

OTHER PUBLICATIONS

U.S. patent application Ser. No. 07/511,341 dated Apr. 1991 to Harjunmaa et al.

U.S. patent application Ser. No. 07/511,229 dated Apr. 1991 to Mendelson et al.

U.S. patent application Ser. No. 07/527,514 dated May 1990 to Harjunmaa et al.

U.S. patent application Ser. No. 07/725,441 dated Jul. 1991 to Harjunmaa et al.

U.S. patent application Ser. No. 07/725,502 dated Jul. 1991 to Harjunmaa et al.

NONINVASIVE MEASUREMENT OF HEMATOCRIT AND HEMOGLOBIN CONTENT BY DIFFERENTIAL OPTICAL ANALYSIS

RELATED APPLICATIONS

The following are related applications: U.S. Ser. No. 07/511,341 filed Apr. 19, 1990 entitled "Method and Apparatus for Measuring the Concentration of Absorbing Substances"; U.S. Ser. No. 07/511,229 filed Apr. 19, 1990 entitled "Method and Apparatus for Monitoring Blood Analytes Noninvasively by Pulsatile Photoplethysmography"; U.S. Ser. No. 07/527,514 filed May 23, 1990 entitled "Method for Determining by Absorption of Radiations the Concentration of Substances in Absorbing and Turbid Matrices"; U.S. Ser. No. 07/725,502 filed Jul. 3, 1991 entitled "Electromagnetic Method and Apparatus to Measure Constituents of Human or Animal Tissue" and U.S. Ser. No. 07/725,441 filed Jul. 3, 1991 entitled "Electromagnetic Method and Apparatus to Measure Constituents of Human or Animal Tissue", each of which is incorporated by reference herein.

FIELD OF THE INVENTION

This invention relates generally to optical systems used for the measuring properties of materials in suspension in fluids. In particular, this invention relates to the noninvasive measurement of blood hematocrit and hemoglobin content. Hemoglobin content is a measure of the quantity of hemoglobin in a given volume of blood. Hematocrit is a relative measure of the volume percentage of erythrocytes versus the total volume of blood. Both variables are used for diagnoses of various cardiovascular and pulmonary abnormalities.

BACKGROUND OF THE INVENTION

Optical oximetry, which is based upon the difference in the absorption properties of oxyhemoglobin and deoxyhemoglobin, was used by Donahoe et al. to measure tissue, as well as arterial oxygen saturation. ("A New Noninvasive Backscattering Oximeter", T. M. Donahoe and R. L. Longini, *Proceedings of the IEEE/-Seventh Annual Conference of the Engineering in Medicine and Biology Society*, pp. 144-147, 1985.)

The Donahoe et al. paper describes a noninvasive backscattering oximeter which utilizes photon diffusion theory to analyze the optics of blood in perfused tissue. In backscattering oximetry, a light source and light detector are placed side by side on the same tissue surface, whereas in transmission oximetry, two or more wavelengths of light are transmitted through the tissue and the effect on the transmitted light is measured to evaluate the degree of oxygen saturation of hemoglobin. Specifically, the Donahoe oximeter had the ability to detect changes in the volume of blood cells relative to that of tissue which the authors conveniently defined as "tissue hematocrit". Although "tissue hematocrit" and blood hematocrit may be related, the exact relationship is not known and can not be accurately defined or predicted for each individual. Furthermore, the accepted parameter which is most commonly used in clinical medicine is referred to as "blood hematocrit", which is defined as the volume percentage of erythrocytes in whole blood, and not "tissue hematocrit", as defined by Donahoe, et al. Moreover, the method described by Donahoe, et al. requires careful calibration to correct for variations in tissue scattering and absorption among individuals and among different sites, even on one individual.

The calibration method proposed by Donahoe et al. requires the application of pressure to the tissue site where the measurement is performed in order to render the tissue site bloodless. This calibration procedure results in large errors for two primary reasons: 1) it is difficult to know exactly the amount of blood in the tissue during calibration or whether the tissue was rendered completely bloodless, and 2) the application of pressure to biological tissues deforms the tissue structures which, in turn, results in different optical properties compared to that of the undeformed blood perfused tissue.

Sperinde et al., in U.S. Pat. No. 4,523,279 issued Jun. 11, 1985, disclose an invasive oximeter technique in which light at three different wavelengths is optically integrated and coupled through an optical fiber to an aperture in a distal tip of a catheter disposed within a blood vessel. Back-scattered and reflected radiation is received through a separate optical fiber to a second aperture in the tip and coupled to a central processor. Blood oxygen saturation is measured as a function of the radiation intensities from the back-scattered light at the three different wavelengths normalized with respect to a reference light intensity measurement.

Takatani et al., in U.S. Pat. No. 4,867,557 issued Sep. 19, 1989, disclose a non-invasive reflection type oximeter which requires light beams at six different wavelengths to be applied to the body tissue. Light received from the six different beams, after being absorbed in the tissue, is detected by a single detector and processed in accordance with a predetermined function to determine the quantity of hemoglobin and oxygen saturation of the body tissue. A light interception barrier separates the transmit light beams from the single light receiving element to prevent direct light cross-talk (or coupling) of light on the receiving element. This oximeter is directed to body parts which do not contain a pulsatile component and requires constant light intensity.

SUMMARY OF THE INVENTION

A need exists for a relatively simple non-invasive method of simultaneous measurement of hemoglobin content and hematocrit in tissue. Various noninvasive spectrophotometric methods for measuring biochemical variables in tissues and blood are based on light transmission through, or reflection from, peripheral tissues. The measurement of biochemical variables, such as glucose, oxygen, bilirubin and other important physiological variable, are essential for clinical diagnosis. Variations in several biochemical substances in the body has a direct effect on the shape of the red blood cells. This, in turn, will change the hematocrit of the blood and cause a change in the optical absorption properties of the blood and tissue when attempting to perform noninvasive measurements through the skin. For example, variations in blood glucose and salt concentrations can cause the red blood cells to change their volume and shape due to changes in the hypotonicity or hypertonicity of the plasma in which the red blood cells are suspended. Since these changes have a direct effect on the optical scattering properties of the tissue, large errors occur when trying to quantify relatively small changes in the concentration of various biochemical analytes in the blood from changes in the optical absorption of tissue using transmission or reflection spectroscopy. The present invention overcomes this problem by providing a method to compensate for undesired variations in blood hematocrit or hemoglobin concentration within the optical path. The method can also be used to independently measure blood hematocrit or hemoglobin concentration noninvasively.

The present invention is based on photoplethsmography, which is the study of volume changes in the body. In particular, the relative magnitude of the photoplethysmographic signal measured, at different times of the cardiac cycle, with two different wavelengths, each detected by two spatially separated photodetectors, is utilized to determine blood hematocrit and hemoglobin content.

DETAILED DESCRIPTION OF THE INVENTION

Figure 1:
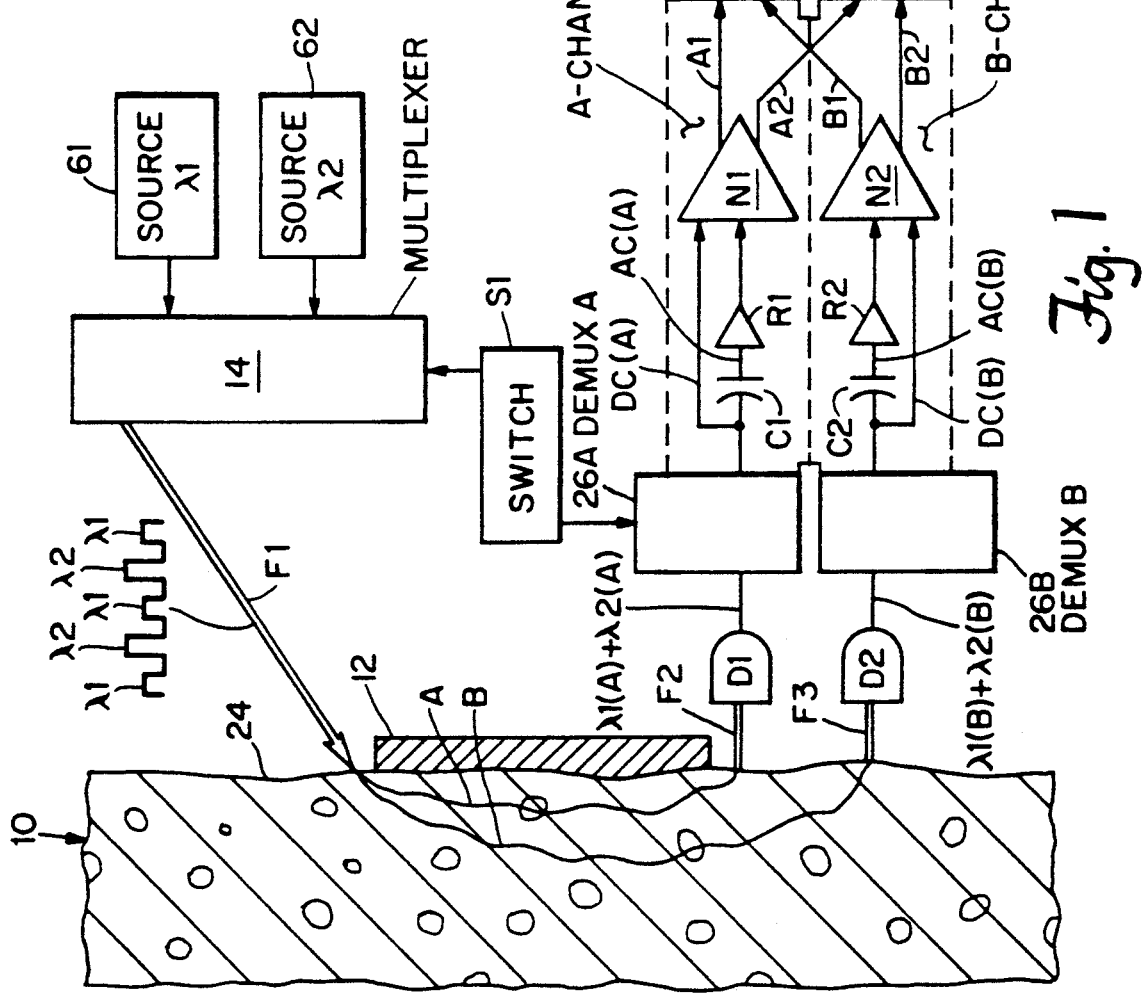
FIG. 1 is a block diagram of a first embodiment of the invention.

FIG. 1 illustrates the invention in detail. A portion of bodily tissue 10, such as the web of the hand between the thumb and index fingers, the forehead or any other portion of the skin, is illuminated by a light beam generated by two sources 61 and 62 of equal or unequal intensity and respective wavelengths $\lambda 1$ and $\lambda 2$. Both wavelengths are selected so as to be substantially insensitive to variations in oxygen saturation or any other blood constituent other than hematocrit or hemoglobin content. The wavelengths 815 nm and 950 nm are preferred examples. Light sources L1 and L2 may comprise fixed or tuneable lasers or LED's. The light from sources L1 and L2 is time multiplexed in multiplexer 14 under control of timing switch S1 to produce a single beam of light comprising time multiplexed pulses $\lambda 1$ and $\lambda 2$. The beam from multiplexer 14 may be butt-coupled to the skin 24 of tissue 10 or may be coupled to the skin by optical fiber F1, as shown. The light beam undergoes scattering and absorption in the tissue according to certain path A or B determined by the constituents in the tissue. Ultimately the light beam exits the tissue either by transmission, transflection or reflection and is detected by detectors D1 and D2 which are shown located for reflectance or transflectance measurement.

By placing the two photodetectors D1 and D2 on or near the surface of the skin 24 at two different locations corresponding to a shorter pathlength A and a longer pathlength B, it is possible to detect two photoplethysmographic waveforms $\lambda 1$ (A) & $\lambda 2$ (A) and $\lambda 1$ (B) & $\lambda 2$(B) corresponding to the light intensities emanating from the tissue 10, respectively. Note: If the detectors are not disposed on the skin, optical fibers F2 and F3 may be used to couple the received light to a respective detector D1 or D2. The detected waveforms are demultiplexed in demultiplexer 26 which is comprised of an A-demultiplexer 26A and a B-demultiplexer 26B to which the respective diode detector outputs are coupled. The demultiplexed signals $\lambda 1$(A) and $\lambda 2$(A) travelling the A-path are coupled to signal processing A-channel. The demultiplexed signals travelling the B-path through tissue 10 ($\lambda 1$ (B) and $\lambda 2$(B)) are coupled to signal processing B-channel. The waveforms demultiplexed in demultiplexers 26A and 26B are synchronized with multiplexer 14 by switch S1. The relative intensities of the four photoplethysmographic waveforms $\lambda 1$(A) & $\lambda 2$(A) and $\lambda 1$(B) & $\lambda 2$(B) is proportional to the separation distances of the two photodetectors D1 and D2, respectively, from the point of entry of the beam into the tissue. An optical shield 12 is placed between the light source 14 (or fiber optic F1) and the two photodetectors D1 and D2, (or fiber optics F1 & F2), in order to eliminate the possibility of detecting light directly coupled between the light source and the photodetectors.

Figure 2:
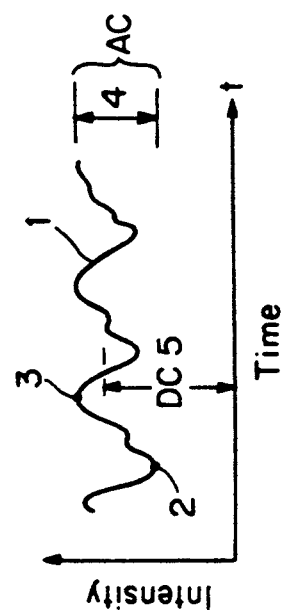
FIG. 2 is a plot of light intensity versus time illustrating the modulation of light intensity by changes in arterial blood volume each time the heart contracts.

The light intensity absorbed by the tissue 10 is modulated by the change in arterial blood volume each time the heart contracts. FIG. 2 is a plot of the intensity detected by one of the detectors versus time after it has been time demultiplexed. When more blood is present in the tissue during peak systole (point 2), more light will be absorbed and less light will be detected by the photodetector. Likewise, during peak diastole (point 3), less blood will be present in the tissue, and the photodetectors will detect a stronger signal. The relative magnitude of this signal, which is given by the peak-to-peak value of the photoplethysmographic waveform 4, is a function of the incremental amount of blood that enters the tissue during systole with each heart beat. In addition to the time variant (AC) component of the photoplethysmogram, which is a function of the incremental increase in blood volume during systole, there is also a time-invariant (DC) component (5) in the photoplethysmogram. This DC component corresponds to the average amount of blood present in the tissue between heart beats and is also proportional to the amount of light Io entering the tissue. The detected optical photoplethysmogram waveforms $\lambda 1$(A) & $\lambda 2$(A) and $\lambda 1$(B) & $\lambda 2$(B) after conversion into electrical intensity signals by respective detectors D1 and D2 and demultiplexing in 26A and 26B are separated into AC waveform components AC(A) and AC(B) by blocking capacitors C1 and C2. These AC components are subsequently converted into respective DC voltages corresponding to the amplitude of the photoplethysmographic signals by respective rectifiers and (if necessary amplifiers) R1 and R2. The DC components DC(A) and DC(B) are coupled directly to respective normalization circuits N1 and N2 along with the outputs from R1 and R2.

The magnitude of each photoplethysmogram is normalized by dividing its AC component by its DC component in the normalization circuits N1 and N2. This cancels out the effect of variations in the output light intensity of the light sources used to illuminate the tissue 10. By calculating the ratios between the normalized magnitudes of the two photoplethysmograms detected by the two differently spaced photodetectors in ratio circuits 16A and 16B, a relationship is obtained which provides information on the total hemoglobin content present in the tissue and hematocrit. The ratio between $A_1$ and $B_1$ (one pair of outputs of the normalization circuit $N_1$ and $N_2$) is computed by the ratio circuit 16A and this value, which is computed for $\lambda 1$ (or 850 nm), is empirically correlated against hemoglobin content to provide a mathematical relationship for predicting hemoglobin content values.

In like manner, the de-multiplexed $\lambda 2$(A) and $\lambda 2$(B) signals for the second wavelength $\lambda 2$ are then processed in the same manner in channels A and B, respectively, to produce a second set of normalized photoplethysmograms A2 and B2. The second wavelength, $\lambda 2$ (for example 950 nm) is not only sensitive to variations in hemoglobin, but is also sensitive to variations in the plasma content in the tissue. This wavelength may be used to obtain hematocrit information, as indicated above. The scattered and absorbed light from λ2 is also detected in detectors D1 and D2 and split into DC and AC components AC(B) and DC(B) by rectifying amplifying and filtering, as above in R1 and C1 and R2 and C2. This process provides information on the optical absorption of tissue as a function of the total light absorbed by both hemoglobin and plasma. The ratio of the normalized AC/DC components A2/B2 of each photoplethysmogram detected at respective wavelength λ2 is empirically correlated against known hematocrit values to find a mathematical relationship for predicting hematocrit values. It is thus possible to obtain a quantitative measure of hemocrit by computing the relative concentrations of hemoglobin content to plasma content. Data processor 20 has stored in it the aforesaid mathematical relationship to provide an absolute indication of blood hematocrit and hemoglobin content noninvasively. These values may be displayed on display 22.

An example of a mathematical relationship which could be stored in the data processor 20 is as follows:

$$\text{Hemoglobin Content} = K_0 + K_1 \left(\frac{A_1}{B_1}\right) + K_2 \left(\frac{A_1}{B_1}\right)^2$$

$$\text{Hematocrit} = K_3 + K_4 \left(\frac{A_2}{B_2}\right) + K_5 \left(\frac{A_2}{B_2}\right)^2$$

Where $K_0$, $K_1$, $K_2$, $K_3$, $K_4$ and $K_5$ are six empirically determined regression coefficients. These coefficients can be determined by a calibration study in which $$\frac{A_1}{B_1} \& \frac{A_2}{B_2}$$

are measured in different patients having different known hemoglobin content and hematocrit values. These values may have been obtained by prior in vivo or in vitro tests. After these six coefficients are determined, they are permanently programmed into the data processor (20) and used to predict hemoglobin content and hematocrit by measuring the values of $$\frac{A_1}{B_1} \text{ and } \frac{A_2}{B_2}$$

in the patient under test.

Equivalents

Those skilled in the art will recognize, or be able to ascertain, using no more than routine experimentation, many equivalents to the specific embodiments of the invention described herein.

The invention is not limited to the two wavelengths (815 and 950 nm). It is only necessary that one wavelength be used that is not absorbed by the plasma but is absorbed by the hemoglobin (this can be done by the 815 nm wavelength) for computing hemoglobin content. For computing hematocrit, a second wavelength is required that is absorbed by both hemoglobin and plasma (such as 950 nm).

Figure 3:
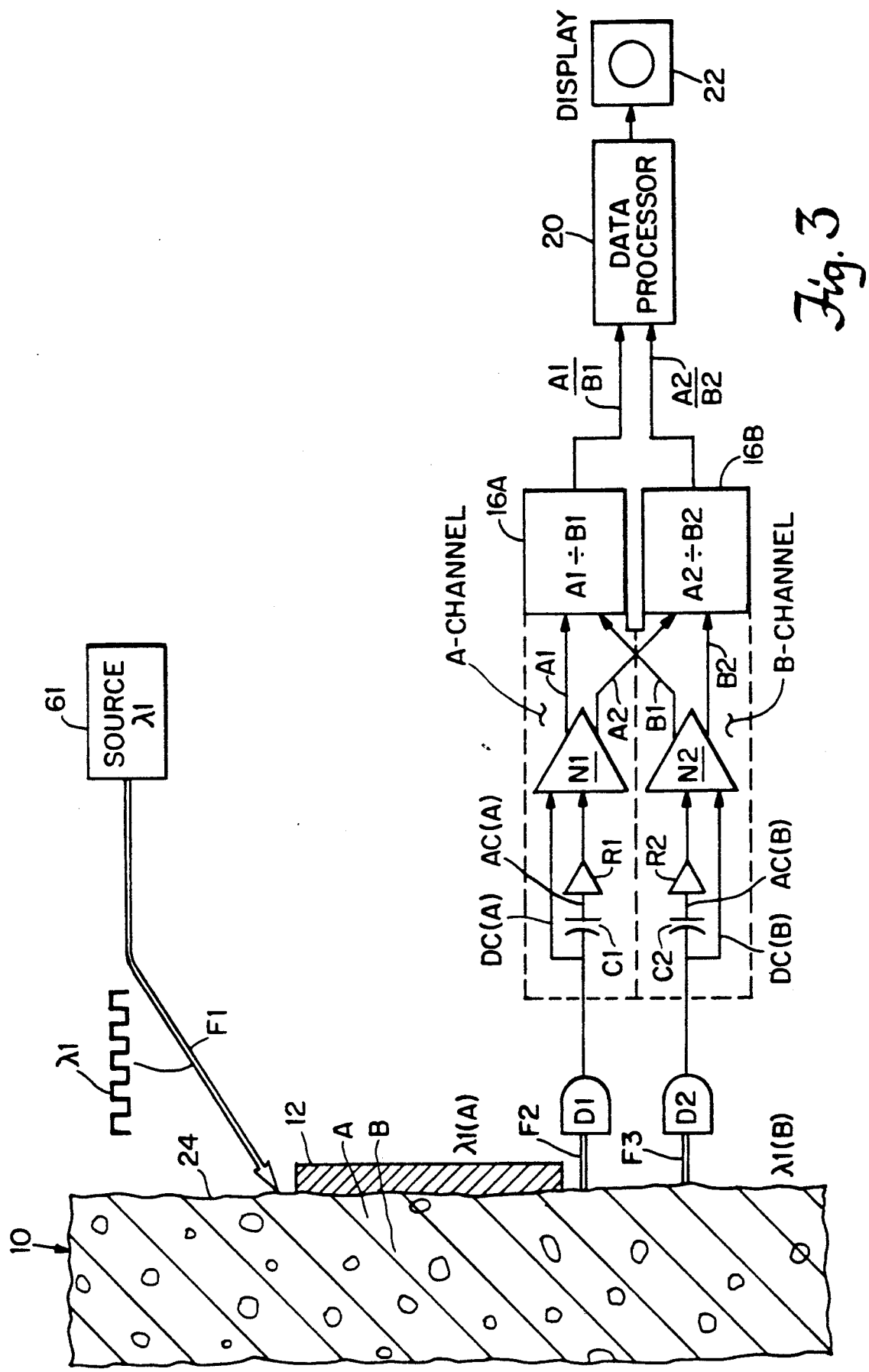
FIG. 3 is a block diagram of a second embodiment of the invention in which a single wavelength input signal is employed.

An alternate embodiment of a single wavelength embodiment invention is shown in FIG. 3 wherein components common to FIG. 1 retain the same numerical designation. In this embodiment only a single wavelength λ1 is needed in order to generate the two ratio signals A1/B1 and A2/B2 processed in processor 20. Otherwise, the function and operation are as previously discussed in connection with FIG. 3.

Rather than multiplexing and demultiplexing the illuminating signals at wavelengths λ1 and λ2, two sets of input optics and processing optics and detectors and processor channels may be operated in parallel.

These and all other equivalents are intended to be encompassed by the following claims.

I claim:

1. A noninvasive method of generating a ratio of signals from which measurement of one or more blood parameters in living tissue may be made, comprising the steps of:
   a) illuminating the tissue with light of a first wavelength λ1 at an incident tissue site, such that the light is scattered and absorbed by the tissue;
   b) while the volume of blood in the tissue is changing, detecting the scattered light at two separate detection tissue sites remote from said incident site and generating first and second electrical signals proportional to the intensity of the detected light;
   c) normalizing the first and second electrical signals to produce first and second normalized signals; and
   d) forming a ratio of the first and second normalized signals.

2. The method of claim 1 wherein λ1 is about 815 nm and the blood parameter measured is hemoglobin.

3. The method of claim 1 wherein the volume of blood is changing due to a cardiac cycle, such that the first and second electrical signals represent photoplethysmographic waveforms.

4. The method of claim 1 wherein the parameter measured is hemoglobin and the wavelength λ1 is a wavelength which is insensitive to all tissue parameters except hemoglobin.

5. A method of noninvasive measurement of predetermined blood constituents in living tissue comprising the steps of:
   a) illuminating the tissue with light of a first wavelength λ1 at an incident tissue site S1, such that the light is scattered and absorbed in the tissue;
   b) while the volume of blood in the tissue is changing, detecting the illuminated light, after it is scattered and absorbed at two separate tissue sites remote from the incident site and generating first and second electrical signals proportional thereto;
   c) separating a respective DC component of the first and second electrical signals from a respective AC component of the first and second electrical signals;
   d) dividing the AC component of the respective first and second electrical signals by the DC component of the first and second electrical signals to produce a respective normalized first and second electrical signals;
   e) forming a ratio by dividing the normalized first signal by the normalized second signal; and
   f) comparing said ratio with a predetermined value to determine the relative concentration of a predetermined blood constituent in the tissue.

6. The method of claim 5 wherein the predetermined blood constituent is hemoglobin content and λ1 is a wavelength chosen to be relatively insensitive to tissue constituents other than hemoglobin content.

7. The method of claim 6 wherein an optical shield is disposed between the incident site and the detection sites to prevent non-scattered light from being detected.

8. The method of claim 6 wherein λ1 is about 815 nm.

9. The method of claim 5 wherein the blood volume in the tissue is changing due to a cardiac cycle.

10. Apparatus for noninvasive generation of a ratio signal for measurement of blood parameters in living tissue comprising:

a) a light source for illuminating the tissue with light of a first wavelength λ1 at an incident tissue site, such that the light is scattered and absorbed by the tissue;

b) light detectors for detecting the scattered light from λ1 at two separate detection tissue sites remote from said incident site and generating first and second electrical signals proportional to the intensity of the detected light;

c) normalizing means for normalizing the first and second electrical signals to produce first and second normalized signals; and d) ratio means for forming a ratio of the first and second normalized signals.

11. The apparatus of claim 10 wherein λ1 is about 815 nm.

12. The apparatus of claim 10 including a signal processor in which the ratio derived in part (d) is processed to produce a measure of blood hemoglobin.

* * * * *